United States Patent [19]

Leuvering

[11] 4,313,734
[45] Feb. 2, 1982

[54] METAL SOL PARTICLE IMMUNOASSAY

[75] Inventor: Johannes H. W. Leuvering, Heesch, Netherlands

[73] Assignee: Akzona Incorporated, Asheville, N.C.

[21] Appl. No.: 57,309

[22] Filed: Jul. 13, 1979

[30] Foreign Application Priority Data

Jul. 13, 1978 [NL] Netherlands .......................... 7807532

[51] Int. Cl.³ ...................... G01N 33/54; G01N 33/58
[52] U.S. Cl. ................................. 23/230 B; 252/408; 422/61; 424/12
[58] Field of Search ........................ 23/230 B; 424/12; 422/61; 252/408

[56] References Cited

U.S. PATENT DOCUMENTS

| | | | |
|---|---|---|---|
| 3,551,555 | 12/1970 | Schuurs | 424/12 |
| 3,933,997 | 1/1976 | Hersh | 23/230 B X |
| 3,970,518 | 6/1976 | Giaever | 23/230 B X |
| 4,018,886 | 4/1977 | Giaever | 23/230 B X |
| 4,020,151 | 4/1977 | Bolz | 23/230 B X |
| 4,067,959 | 1/1978 | Bolz | 23/230 B X |
| 4,108,972 | 8/1978 | Dreyer | |
| 4,177,253 | 12/1979 | Davies | 23/230 B X |
| 4,205,952 | 6/1980 | Cais | 23/230 B |
| 4,219,335 | 8/1980 | Ebersole | 23/230 B |

OTHER PUBLICATIONS

J. H. W. Leuvering, P. J. H. M. Thal, M. v.d. Waart and A. H. W. M. Schuurs, "Sol Particle Agglutination Immunoassay for Human Chorionic Gonadotrophin", Fresenius Z. Anal. Chem. Band 301 at 132 (1980).
M. Horisberger et al., Experientia, 31/10, 1147–1149 (Oct. 1975).
Chemical Abstracts, 82:14952s (1975).
E. L. Romano et al., Immunochemistry, 11, 521–522 (1974).
Chemical Abstracts, 88:150306k (May 1978).
R. S. Molday et al., Nature, 249, 81–82 (1974).
J. H. W. Leuvering, et al., "Sol Particle Immunoassay (SPIA)", J. Immunoassay 1 (1) at 77–91 (1980).
E. L. Romano, Martha Romano, "Staphylococcal protein A bound to colloidal gold: A useful reagent to label antigen-antibody sites in electron microscopy", Immunochemistry, 14 (9–10) at 711–715 (1977).
G. A. Ackerman, et al., "Surface Distribution of Monosialoganglioside GM1 on human blood cells and the effect of exogenous GM1 and neuranimidase on chlorera toxin surface labeling: A quantitative immunocytochemical study", J. Histochem. Cytochem. 28 (10) at 1100–1112 (1980).
Faulk, W. P.; Taylor, G. M., "An Immumocolloid method for the electron microscope." Immunochem. 8, 1971, 1081–1083.
Gerber, H.; Horisberger, M; Bauer, H., "Immunosorbent for the isolation of specific antibodies against man- Horisberger, M; Rosset, J., "Localization of wheat germ agglutinin receptor sites on yeast cells by scanning electron microscopy." Experientia 32, 1976, 998–1000.
Horisberger, M.; Rosset, J., "Colloidal gold, a useful marker for transmission and scanning electron microscopy." J. Histochem. Cytochem. 25, 1977, 295, 305.
Roth, J.; Binder, M., "Colloidal gold, ferritin and peroxidase as markers for electron microscopic double labeling lectin techniques." J. Histochem. Cytochem. 26, 1978, 163–169.
Horisberger, M.; Rosset, J.; Buaer, H., "Localization of mannan at the surface of yeast protoplasts by scanning electron microscopy." Arch. Microbiol. 109 1976, 9–14.
Horisberger, M.; Rosset, J.; Buaer, H., "Colloidal gold granules as markers for cell surface receptors in the SEM." Experientia 31, 1975, 1147–1149.
Horisberger, M.; Rosset, J.; Vonlanthen, M., "Location of lectin receptors on rat hepatocytes by transmission and scanning electron microscopy." Experientia 34, 1977, 274–276.
Roth, J.; Wagner J., "Peroxidase and gold complexes of lectins for double labeling of surface binding sites by electron microscopy." J. Histochem. Cytochem. 25, 1977, 11–81–1184.
Georghegan, W. D.; Ackerman, G. A., "Adsorption of horseradish peroxidase, ovomucoid and anti-immunoglobulin to colloidal gold for the indirect detection of concanavalin A, wheat germ agglutinin and goat anti-human immunoglobulin G on cell surfaces at the electron microscopic level; a new method, theory and application." J. Histomchem. Cytochem. 25, 1977, 1187–1200.
Frens, G., "Controlled nucleation for the regulation of particle size in monodisperse gold suspensions." Nature Phys. Sc. 241, 1973, 20–22.
Feldherr, C. M.; Marshall, J. M., "The use of colloidal gold for studies of intracellular exchanges in ameba chaos chaos." J. Cell Biol. 12, 1962, 640–645.
S. L. Goodman, "Colloidal Gold Probes–A Further Evaluation", Scanning Electron Microscopy 3 at 619–627 (1979).
Geoghegan, William D., et al., "Passive Gold Agglutination. An Alternative to Passive Hemagglutination", J. Immunological Methods 34 at 11–21 (1980).
M. S. Shahrabadi et al., "A Method for Staining Intracellular Antigens in Thin Sections with Ferritin-Labeled Antibody", J. Cell. Biol. 50 at 246–250 (1971).
Romano, E. L.; C. Stolinski and N. C. Hughes-Jones, Br. J. Haematol. 30 at 507 (1975).
Horisberger, M.; Farr, D. R.; Vonlanthen, M., "Ultrastructural localization of beta-D-galactan in the nuclei of the myxomycete, Physarum polycephalum." Biochim. Biophys. Acta. 542, 1978, 308–314.
M. Cais et al., Nature, vol. 270, 534–535 (Dec. 8, 1977).

*Primary Examiner*—Sidney Marantz
*Attorney, Agent, or Firm*—Robert H. Falk; Charles A. Wendel; Frank W. Young

[57] ABSTRACT

A method, test kit and labeled component for the detection and/or determination of one or more components of the reaction between a specific binding protein and the corresponding bindable substance, in which one or more labelled components are used, that are obtained by coupling particles of a dispersion of a metal, metal compound or polymer nuclei, coated with a metal or metal compound, having a particle size of at least 5 nm, directly or indirectly to the desired component of said reaction.

During the reaction or after an adequate reaction time, the physical properties and/or the amount of the metal and/or the formed metal containing agglomerate, is/are determined in the test sample, or optionally after a separation of the bound and free metal-labelled components in one of the derived fractions by methods known as known by those skilled in the immunoassay field.

48 Claims, No Drawings

METAL SOL PARTICLE IMMUNOASSAY

BACKGROUND OF THE INVENTION

1. Field of the Invention

The invention relates to a method for the detection and/or determination of one or more components of the reaction between a specific binding protein and the corresponding bindable substance in an aqueous test sample, by applying the known binding affinity of such components for one another. Such components can be receptor proteins or immunochemical components, such as haptens, antigens or antibodies.

2. Description of the Prior Art, and Other Information

There are a large number of immunochemical methods known in which the presence of a certain immunological component is determined qualitatively and/or quantitatively by utilizing the mutual reactions between such components, such as the reaction between antigen and the antibody to that antigen.

In the study of such reactions for the demonstration and/or determination of the desired component, use may be made of aids, for example physical aids such as an electron microscope, or use may be made of a reagent which is provided with a marker or label which can be determined or demonstrated respectively in a lower concentration than the immunocomplex formed itself.

As examples of the category of qualitative immunochemical techniques there may be named the immunodiffusion method developed in 1948 by Ouchterlony and the variant thereof, immuno-electrophoresis, developed in 1953 by Grabar. The radial immunodiffusion method developed by Mancini in 1965 can be used quantitatively.

The immunodiffusion technique can be characterized as the placing of a thin layer of agar on a glass plate, after which two holes are made in the gel, a little distance apart. The test liquid with antigen is introduced into one of the holes, and an antiserum into the other. As a result of the diffusion of the two substances in the gel, these meet each other and form a visible precipitation line. Though this method is relatively simple, it does possess a number of disadvantages, in particular the fact that the diffusion lasts for some time and that the results usually only provide a qualitative indication. The other immunochemical techniques also have their drawbacks, which apart from specific disadvantages generally consist of too long a duration for the test, a low sensitivity and/or the provision of only qualitative indications.

In addition to these non-labelled immunochemical techniques, a number of labelled techniques have been developed with the passage of the years, amongst which there may be named the haemagglutination test in which one of the components is bound to the surface of erythrocytes; the immunofluorescence technique, in which one of the components is labelled with a fluorescent compound (fluorophore); the radio-immunological determination developed by Yalow and Berson about 1959, in which, instead of a fluorophore, a radio-active atom or radio-active group is used as marker; and the most recent technique of enzyme-immunological determination, about which the first publications appeared in 1971 from two groups working independently, namely the Swedish investigators Engvall and Perlmann and the Dutch Schuurs and van Weemen. This last-named determination is in principle analogous to the known radio-immunological determinations, but with the difference that an enzyme is used as label instead of radio-active labelling.

The much-used radio-immunological determination has indisputably great merit, but there are a number of substantial drawbacks associated with this method, such as the risk factor related to working with radio-active material, the high costs of reagents and apparatus, the poor stability of radio-active labelled reagents and the requirement that only qualified personnel be allowed to perform these determinations.

The enzyme-immunological determination method does not possess these disadvantages, but it is nevertheless desirable that new estimation techniques be developed which are even more sensitive, may be performed more rapidly, can be more readily automated and/or make it possible to estimate more than one immunocomponent at the same time.

Furthermore, there is a strong need for a reliable and practical assay for receptor proteins.

SUMMARY OF THE INVENTION

The present invention relates to a process for the detection and/or determination of one or more components of the reaction between a specific binding protein and the corresponding bindable substance in an aqueous test sample, by applying the known binding affinity of such components for one another, which is characterized by the fact that one or more labelled components, obtained by coupling directly or indirectly the desired component of said reaction to particles of an aqueous dispersion of a metal, metal compound or polymer nuclei coated with a metal or metal compound, having a particle size of at least 5 nm, whereby during the reaction or after an adequate reaction time, optionally after separation of the bound and free labelled components, the physical properties and/or the amount of the meal and/or the formed metal containing agglomerate is/are determined in the test sample or one of the derived fractions, by methods known to those in the art, which determination provides a qualitative and/or quantitative indication of the component or components to be detected and/or determined.

The process according to the invention is especially suited for the estimation of immunochemical components, such as haptens, antigens and antibodies.

The particles of the aqueous dispersion of a metal, metal compound or polymer nuclei, coated with a metal or metal compound have a particle size of at least 5 nm and preferably 10 to 100 nm. Dispersions with a particle size of 10 to 100 nm of the dispersed phase are usually sols, but other types of dispersions are not excluded.

The component to be labelled is coupled directly or indirectly to the dispersed particles. Under coupling is understood any chemical or physical binding, such as binding via covalent bonds, via hydrogen bridges, polar attraction and adsorption.

Whenever the term "metal sol particles" is used in the text which follows, this is understood to signify particles of a sol, consisting of a metal, a metal compound or polymer nuclei coated with a metal or metal compound.

DESCRIPTION OF THE PREFERRED EMBODIMENTS

The use of metal sol particles, in particular those of gold sols, which are covered on the surface with antibodies, for the demonstration of the distribution of an antigen over a cell surface by means of scanning electron microscopy, in which the metal sol particles are used as contrast enhancing label, has already been described some years ago (see article by M. Horisberger in Experientia, pages 1147–1149, 15th October 1975), but the application of dispersed particles, perferably metal sol particles as a label for an immunological component for an in vitro qualitative and quantitative determination of immunological components, such as haptens, antigens and antibodies, in an aqueous test medium has not previously been reported and has surprisingly proved to be possible.

The metal sol particle immunochemical technique according to the instant invention which has been developed can be not only more sensitive than the known radio- and enzyme-immuno techniques, but renders it furthermore possible to demonstrate and to determine more than one immunological component in the same test medium simultaneously by utilizing sol particles of different chemical composition as labels.

The metal sols may be of metals or metal compounds, such as metal oxides, metal hydroxides and metal salts or of polymer nuclei coated with metals or metal compounds. As examples, there may be named the metals platinum, gold, silver and copper, and the metal compounds, silver iodide, silver bromide, copper hydrous oxide, iron oxide, iron hydroxide or hydrous oxide, aluminum hydroxide or hydrous oxide, chromium hydroxide or hydrous oxide, vanadium oxide, arsenic sulphide, manganese hydroxide, lead sulphide, mercury sulphide, barium sulphate and titanium dioxide. In general all metals or metal compounds, which may be readily demonstrated by means of known techniques.

It is sometimes advantageous to use sols with dispersed particles consisting of polymer nuclei, coated with the above mentioned metals or metal compounds. These particles have similar properties as the dispersed phase of pure metals or metal compounds, but size, density and metal contact can be optimally combined.

Use is preferably made of metals or metal compounds which are not or in very small quantities present in the test medium, in particular of those metals or metal compounds which have a low detection limit in suitable analysis techniques.

The metal sol particles to be used as label may be prepared in a large number of ways which are in themselves known. For example, for the preparation of a gold sol reference is made to an article by G. Frens in Nature Physical Science 241, 20 (1973).

The metal sol particles carry a charge which confers a stabilizing effect by mutual repulsion. By addition of chiefly strong electrolytes, the charge pattern is changed, as a result of which aggregation and flocculation occurs. This may be prevented by coating the particles with macromolecules processing polar groups, such as proteins, polyethylene glycols, polymeric carbohydrates, polyvinyl alcohols and similar.

As protective proteins, it is possible to use antigens, antibodies and anti-antibodies, or immunochemically active fragments thereof, or haptens that have been coupled to immunochemically inert, protective macromolecules, which results directly in immuno-components labelled with metal sol particles.

It is not necessary that immuno components are used exclusively for the coating of the metal sol particles, since though this does provide a stabilizing effect, the immunochemical reactivity may be less than expected, probably due to steric hindrance. It has therefore also proved advantageous to coat only partially with an immunocomponent, and to complete the coating with another protective, but immunochemically inert, material, such as inert proteins, for example albumin, a polyethylene glycol, or another polar macromolecule. As coating material, use may also be made of proteins A or related proteins, which possess reactivity with respect to the Fc part of antibodies. After the coating of the metal sol particles with protein A, a further coating may be brought about with a selected antibody.

Another possibility consists of first coating the metal sol particles with an inert hydrophilic macromolecule, e.g. a polymer or co-polymer, after which the immunological component is coupled to the coating material by adsorption or by covalent binding.

The globules obtained after coating may contain a single metal sol particle, but it is also possible that the polymer encloses more than one metal sol particle.

The coating of the metal sol particles by the inert polymer may take place in two ways, either by bringing the metal sol into contact with the polymer or by introducing the metal sol into an environment containing a monomer, or various monomers, and causing these to polymerize or co-polymerize respectively in situ. The polymerization can be initiated under the influence of radiation, or by the addition of initiators, such as a persulphate.

The coating of a metal sol particle by polymerization of the monomeric medium in which the particle is located, under the influence of an inorganic initiator such as a persulphate, meets with practical difficulties, since the sol flocculates on addition of such an initiator. It has now been found that such a coating is however possible by first protecting the metal sol particles, then introducing the protected particles into a monomeric medium, and after that finally initiating the polymerization. The compounds mentioned above merit consideration as protective material.

The components labelled with metal sol particles are used as a reagent, generally in combination with other reagents for the demonstration and quantification or receptor proteins and haptens, antigens and antibodies in an aqueous test medium, for which all sorts of immunochemical techniques, in use in radio-immuno and enzyme-immuno tests, receive consideration.

The invention therefore also relates to test-kits for use in such immunochemical techniques, which contain as the most important component a metal-labelled immunocomponent, consisting of a metal sol, the particles of which have either been directly coated by the desired immunocomponent, or have been coated by an inert macromolecule, onto which the immunocomponent has been coupled or adsorbed.

One of the usual immunochemical techniques is the competitive immunotest, which can be used for the demonstration and estimation of every immunocomponent. For the demonstration, for example, of a certain antigen this method consists of bringing a test sample, containing an unknown quantity of antigen, into contact with either a certain amount of the metal-labelled antigen concerned and an insolubilized antibody against this antigen, or a certain amount of insolubilized antigen and a metal-labelled antibody against this antigen.

After an adequate reaction time, the nature and/or the amount of the metal is determined in the bound or free fraction, which gives a qualitative or quantitative indication respectively of the antigen to be determined.

With due changes in the details, an analogous method applies to the determination of other immunocomponents.

The so-called Sandwich techniques are also much used. These are also particularly suitable for the use of a metal-labelled component according to the invention. According to these techniques, an immunological component, for example an antibody if an antigen has to be determined, is rendered insoluble by coupling to a solid carrier. This solid carrier is for example the interior surface of the reaction vessel in which the immunochemical reaction is performed. After an initial incubation, optionally followed by a washing step, a second incubation with a metal-labelled antibody takes place, after which the metal is determined in the bound or the free phase. It is advantageous to determine the metal in the bound phase. In this case after the separation of phases, the bound label is preferably disengaged so that the metal can be determined in the obtained liquid.

Furthermore, a homogeneous agglutination can be used. If the test sample contains the immunochemical component to be determined, agglutination occurs with the labelled immunochemical component, resulting in a change of optical properties. A qualitative or semi-quantitative result can be obtained by observation of the colour change. It is also possible to observe the coarse of the reaction with a spectrophotometer.

In addition to the above-noted techniques, there are numerous other immunochemical techniques in which the metal-labelled immunocomponents can be used as reagent. The present invention also makes it possible to demonstrate different haptens, antigens, antibodies or combinations thereof at the same time in one test sample, by using as reagent for each of the components to be demonstrated an immunocomponent which has been labelled with a different metal sol particle.

The measurement of the physical properties and/or the concentration of the metal and/or the formed metal containing agglomerate in a certain phase of the reaction mixture may take place using numerous techniques, which are in themselves known. As examples of these techniques there may be cited the colorimetric determination, in which use is made of the intense colour of some dispersions which furthermore change colour with physicochemical changes; the visual method, which is often already applicable to qualitative determinations in view of the above-noted fact that metal sols are coloured; the use of flame emission spectrophotometry or another plasma-emission spectrophotometric method which renders simultaneous determination possible, and the highly sensitive method of flame-less atomic absorption spectrophotometry.

The invention is also related to test kits to be used for the determination of one or more components of the reaction between a specific binding protein and the corresponding bindable substance in an aqueous medium, comprising:

(a) a metal labelled component which has been obtained by coupling a component of said reaction to particles of an aqueous dispersion of a metal, metal compound or polymer nuclei coated with a metal or metal compound, which particles have a size of at least 5 nm; and (b) other reagents.

Preferably the test kit contains a metal labelled component, consisting of a sol, having particles with a size varying from 10-100 nm, which are either directly coated by the component of said reaction or by an inert polymer, to which the desired component has been coupled.

The metal-labelled component of the test kit according to the invention can be a metal-labelled immunocomponent. The metal-labelled component can be present as a dispersion, but it appeared to be surprisingly possible to obtain a stable freeze-dried product, that can be redispersed before use. The freeze-dried metal-labelled component can also contain the buffer substance, that is required for carrying out the reaction between the specific binding protein and the corresponding bindable substance.

The invention is further illustrated by means of the following examples.

EXAMPLE I

Colorimetric determination of human placental lactogen (HPL) with the aid of an antibody, labelled with gold particles, from a rabbit anti-HPL serum.

1.1. Preparation of the Gold Sol 500 ml of a 0.10 g/l chloro-auric acid ($HAuCl_4$) solution in distilled water is heated to boiling point in a beaker of 800 ml capacity. 3.5 ml of a 10 g/l solution of tri-sodium citrate in distilled water is introduced into the boiling solution, after which the gold sol, which has become dark red after an initial blue color, is boiled for a further 15 minutes. After cooling to room temperature, the red gold sol thus obtained is made up to a volume of 500 ml with distilled water in a volumetric flask. The gold sol obtained in this way consists of gold particles with diameters between 45 and 70 nm, as verified by electron microscopy. A gold sol prepared in this way has a pH of $3.45 \pm 0.07$ and a light-absorption maximum at 536 nm, while $A_{536\ nm}^{1\ cm} = 1.15 \pm 0.03$.

1.2. Preparation of Rabbit Anti-HPL Sera

Anti-HPL sera were prepared by injecting an HPL solution into rabbits according to the following scheme:

| Day | Method of injection | µg HPL | Dissolved in NaCl 9 g/l | with CFA |
|---|---|---|---|---|
| 1 | intramuscular | 100 | 0.5 ml | 0.5 ml |
| 15 | " | 200 | 0.5 ml | 0.5 ml |
| 29 | " | 400 | 0.5 ml | 0.5 ml |
| 43 | intravenous | 200 | 1.0 ml | — |
| 50 | blood sample for determination of the titre of the antiserum in an EIA test. | | | |

The rabbits were bled out as soon as the titre of the antiserum in an EIA HPL test was greater than 1:5000. If this was not the case, the rabbits received an additional injection of 200 µg HPL in 1.0 ml 9 g/l NaCl (intravenous) and the titre of the antiserum was determined again 7 days after this injection. The antisera were stored at $-25°$ C. or freeze-dried and then stored as a dry powder at $-25°$ C.

1.3. Preparation of the Anti-HPL Immune Globulin Solution From the Rabbit Anti-HPL Serum For this purpose, 600 mg freeze-dried rabbit anti-HPL serum is dissolved in 7.5 ml of an 9 g/l NaCl solution. 10 ml 180 g/l $Na_2SO_4$ solution in distilled water is then added, followed by 1.35 g solid $Na_2SO_4$. The turbid liquid obtained is allowed to stand in a centrifuge tube for 1 hour, after which the liquid is centrifuged at 25000 N/kg for 10 minutes. The supernatant is sucked off and the residue is redispersed in 20 ml of an 180 g/l Na$_2$SO$_4$ solution in distilled water. This procedure is repeated twice.

After the last centrifugation and removal of the supernatant by suction, the residue is dissolved in 20 ml of a 9 g/l solution of NaCl in distilled water. The solution is dialysed against 6 liters dialysis liquid consisting of a 0.3 g/l NaCl solution in distilled water, which has been adjusted to a pH of 7.0 with a solution of 0.2 mol K$_2$CO$_3$ in 1 liter distilled water. Dialysis is continued for 16 hours at 4° C., after which the dialysed liquid is centrifuged at 160000 N/kg for 20 minutes. The immunoglobulin solution is stored in 1 ml vials at a temperature of −20° C.

The immunoglobulin content is determined by measuring $A_{260\ nm}^{1\ cm}$ and $A_{280\ nm}^{1\ cm}$ of a tenfold dilution of the immunoglobulin solution, using a spectrophotometer. The immunoglobulin content G in mg/ml can then be calculated using the formula $G = 10 \times [(1.45 \times A_{280\ nm}^{1\ cm}) - (0.75 \times A_{260\ nm}^{1\ cm})]$.

1.4. Preparation of the Gold Particle—Rabbit Anti-HPL Immunoglobulin Conjugate 500 ml of the gold sol prepared in the way described under 1.1. is adjusted to pH 7.0 by means of a solution of 0.2 mol K$_2$CO$_3$ in 1 liter distilled water. 0.5 ml of the rabbit anti-HPL immunoglobulin solution, with a content of 125 μg immunoglobulin per ml, is added dropwise with vigorous stirring to 25 ml of the neutralized gold sol. 0.5 ml of a 50 g/l solution of bovine serum albumin (BSA) in 5 mmol NaCl/liter is distilled water, which has been adjusted to a pH of 7.0 with a 0.2 mol K$_2$CO$_3$ solution in 1 liter water, is then added, also with stirring.

The gold particle-rabbit anti-HPL immunoglobulin conjugate obtained in this way is centrifuged at 25000 N/kg for 10 minutes, after which the supernatant liquid is sucked off. The red pellet, consisting of the conjugate, is taken up in such a volume (about 23 ml) of trometamol, 0.01 mol/liter adjusted to a pH of 7.4 with 0.01 mol/liter HCl in distilled water (0.01 mol/liter TRIS/HCl buffer, pH=7.4), that the final $A_{536\ nm}^{1\ cm}$ is 1.00.

1.5. Coating of Microelisa(R) Plates with Rabbit Anti-HPL Immunoglobulins

To this end a rabbit anti-HPL immunoglobulin solution is prepared with a content of 25 μg immunoglobulin per ml, in a solution of 0.04 mol Na$_2$HPO$_4$ per liter adjusted to a pH of 7.4 with a solution of 0.04 mol NaH$_2$PO$_4$ per liter, both in distilled water, to which 0.1 g/l Merthiolate has been added.

0.1 ml of the above-described immunoglobulin solution is placed in each well of the Microelisa(R) plate, after which the plate is incubated for 16 hours at 0°-4° C. 0.1 ml 200 g/l BSA solution in a 0.04 mol/l phosphate buffer, pH 7.4, to which 0.1 g/l Merthiolate has been added, is then pipetted into each well, and the whole is incubated for a further 30 minutes at room temperature. The wells of the Microelisa(R) plates are now sucked empty and washed 3 times with distilled water, after which they are kept at −20° C. until use.

1.6. Test Protocol for HPL Estimation with Gold Particle Rabbit Anti-HPL Immunoglobulin Conjugate

1.6.a. Determination of a Standard Curve for HPL

A standard curve was constructed for HPL according to the protocol below.

1. Pipette 0.1 ml of the standard HPL solution into a well of a Microelisa(R) plate coated with rabbit anti-HPL immunoglobulin and incubate for 2 hours at room temperature.
2. Suck the well empty and wash it with 0.1 ml 0.01 mol/l Tris/HCl buffer, pH 7.4.
3. Pipette 0.1 ml gold particle rabbit anti-HPL immunoglobulin conjugate ($A_{536}^{1\ cm} = 1.00$) into the well and incubate overnight at room temperature.
4. Empty the well by suction and wash it with 0.3 ml 0.01 mol/l Tris/HCl/NaCl buffer, pH 7.4.
5. Pipette 0.1 ml 0.1 mol/l HCl solution in water into the well and allow this to act for 30 minutes in the shaker.
6. Measure the light absorption at 536 nm with a small-volume spectrophotometer.

The results of the determination of a standard curve are given in the table below.

| HPL concentration in the standard solution, ng/ml | $A_{536\ nm}^{1\ cm}$ at the end of the test. |
|---|---|
| 0 | 0.030 |
| 0.2 | 0.030 |
| 0.8 | 0.060 |
| 3.2 | 0.106 |
| 12.5 | 0.136 |
| 50 | 0.188 |
| 200 | 0.220 |

The solvent for the HPL standard solution is 0.04 mol/l phosphate buffer + 1 g/l BSA + 9 g/l NaCl, pH 7.4.

1.6.b. Determination of HPL in the Serum of Pregnant Women

The sera of pregnant women were diluted such that the HPL level ranged from 5 to 80 ng/ml. The diluent for the sera was 0.04 mol/l phosphate buffer, pH 7.4 + 1 g/l BSA + 9 g/l NaCl.

With the aid of the test protocol described under 1.6.a., the HPL concentrations of the diluted sera were determined using the standard curve constructed. After correction for the dilution factor, the following results were obtained.

| Serum | HPL content, EIA test | HPL content, MIA |
|---|---|---|
| A | 4.5 ± 0.5 μgμml | 4 ± 1 μgμml |
| B | 3.2 ± 0.4 μg/ml | 3.5 ± 0.8 μg/ml |
| C | 0.7 ± 0.1 μg/ml | 1 ± 0.3 μg/ml |

EXAMPLE II

Determination of HPL with the aid of gold-particle-labelled antibodies and atomic absorption spectrophotometry.

2.1. Preparation of Reagents and Coated Microelisa Plates

The method of preparation of the gold particle rabbit anti-HPL immunoglobulin conjugate and the Microelisa$^{(R)}$ plates coated with rabbit anti-HPL immunoglobulin was the same as described in Example I.

2.2. Test Protocol

2.2.a. Determination of Standard Curve for HPL

In order to construct a standard curve for HPL, serial dilutions of HPL were made of consecutively 1, 10, 100 and 1000 ng/ml and a blank. The solvent for HPL was 0.04 mol/l phosphate buffer, pH 7.4, to which 1 g/l BSA and 9 g/l NaCl had been added.

1. Pipette 0.1 ml standard HPL solution into the well of the coated Microelisa plate and incubate for 2 hours at room temperature.
2. Suck the well empty and wash with 0.1 ml 0.02 mol/l Tris/HCl buffer, pH 7.4.
3. Pipette 0.1 ml of the gold particle anti-HPL antibody conjugate ($A_{536\ nm}^{1\ cm} = 1.00$) into the well and incubate this overnight (about 16 hours).
4. Suck the well empty and wash it with 0.02 mol/l Tris buffer, pH 7.4.
5. Pipette 0.1 ml HCl, 0.1 mol/l, into the well and allow this to act with shaking on a shaking machine for 30 minutes.
6. Now measure the peak value of the light absorption at 242.8 nm in a flame atomic absorption spectrophotometer fitted with a small-volume injector.

A typical example of a standard curve obtained in this way is shown in the table below.

| HPL concentration in standard solution. | Peak value of light absorption at 242.8 nm after termination of the test. |
|---|---|
| 0 ng/ml | 0.020 |
| 1 ng/ml | 0.040 |
| 10 ng/ml | 0.160 |
| 100 ng/ml | 0.200 |
| 1000 ng/ml | 0.220 |

2.2.b. Determination of HPL in the Serum of Pregnant Women

The sera of pregnant women were diluted such that the HPL level lay in the range 5–80 ng/ml. The diluent for the sera was 0.04 mol/l phosphate buffer (pH=7.4)+1 g/l BSA+9 g/l NaCl. With the aid of the test protocol described under 2.2.a., the HPL concentrations of the diluted sera were determined using the standard curve constructed.

EXAMPLE III

Visual detection of hepatitis Bs antigen (HBsAg) by means of gold particle sheep anti-HBs immunoglobulin conjugate.

3.1. Preparation of the Gold Sol

See Example 1.1.

3.2. Preparation of Sheep Anti-HBs Sera

Sheep were injected with purified HBsAg solution.

3.3. Preparation of the Sheep Anti-HBs Immunoglobulin Solution 1.4 g solid $Na_2SO_4$ is added to 10 ml sheep anti-HBsAg serum. After all the sodium sulphate has dissolved, the turbid liquid is allowed to stand for 1 hour at room temperature. The liquid is then centrifuged at 25000 N/kg for 10 minutes. The supernatant is removed by suction and the residue is redispersed in 10 ml 140 g/l $Na_2SO_4$ solution in distilled water. This procedure is repeated twice.

After centrifuging for the last time and removing the supernatant by suction, the pellet is dissolved in 10 ml of 9 g/l NaCl solution in distilled water. This solution is dialysed against 6 liters of a 0.3 g/l NaCl solution for distilled water, adjusted to a pH of 7.0 with a solution of 0.2 mol/l $K_2CO_3$. Dialysis takes place for 16 hours at 4° C., after which the dialysed liquid is centrifuged for 20 minutes at 160000 N/kg.

The immunoglobulin solution is stored in portions of 1 ml in vials at −20° C. The immunoglobulin content is determined by the $A_{260\ nm}^{1\ cm}$, $A_{280\ nm}^{1\ cm}$ method already described.

3.4. Preparation of the Gold-Particle Sheep anti-HBs Immunoglobulin Conjugate The preparation of the conjugate is identical with the method of preparation described in example I point 4, with the exception that a diluted solution (also 125 ng immunoglobulin per ml) of the sheep anti-HBs immunoglobulin solution was used instead of the rabbit anti-HPL immunoglobulin solution.

3.5. Coating of Microelisa$^{(R)}$ Plates with Sheep Anti-HBs Immunoglobulins The coating of Microelisa$^{(R)}$ plates with sheep anti-HBs immunoglobulins is performed in the way described in example I point 5, whereby the sheep anti-HBs immunoglobulin solution was used instead of a rabbit anti-HPL immunoglobulin solution. Ten control wells were included in each plate. These wells were coated with an immunoglobulin solution from human serum which was negative in the following tests:

Hepanosticon and Hepanostika
Monosticon
Rheumanosticon
Immunodiffusion against normal sheep serum
EIA for anti-HBs.

3.6. Test Protocol for a Visually Readable Test

1. Pipette 0.1 ml of the sample into a well of the coated Microelisa plate and incubate for 2 hours at 37° C.
2. Wash each well 3× with 0.3 ml 0.02 mol/l Tris/HCl buffer, pH 7.4.
3. Pipette 0.1 ml gold-particle sheep-anti-HBs conjugate ($A_{536}^{1\ cm} = 1.00$) into the well and incubate overnight at room temperature.
4. Empty the well by suction and wash it 3× with 0.3 ml 0.01 mol/l Tris/HCl/NaCl buffer, pH 7.4.
5. Pipette 0.1 ml 0.1 mol/l HCl solution in distilled water into the well and allow this to act for 30 minutes, on a shaker.
6. Assess visually the color of the liquid in the well and compare it with the control wells present.

Sera which gave a strong positive reaction in the Hepanostika test could generally still be distinguished from the controls in 8-fold dilution.

EXAMPLE IV

Determination of testosterone with the aid of a silver particle testosterone-11α-succinyl-bovine serum albumin conjugate.

4.1. Preparation of the Silver Sol 8.5 ml of a 10 g/l AgNO$_3$ solution in distilled water is diluted with 486.5 ml distilled water and 5.0 ml of a 10 g/l solution of trisodium citrate.2H$_2$O in distilled water is then added. 40.0 ml of a 10 g/l solution of hydrazine in distilled water is added to this solution at room temperature with vigorous stirring using a magnetic stirrer. A grey-yellow-green silver sol with a strong Tyndall scattering is formed within 60 seconds. After 10-fold dilution with distilled water, the pH was 8.85 and the sol had a light absorption of $A_{416\ nm}^{1\ cm} = 0.83$.

20 ml of the undiluted sol was centrifuged for 10 minutes at 25000 N/kg. 15 ml of the supernatant was removed by suction and replaced by 15 ml of a 0.1 g/l trisodium citrate.2H$_2$O solution in distilled water (pH 6.88).

The washing process was repeated twice. After the final washing, the volume was made up to 20 ml with the 0.1 g/l sodium citrate solution.

After 4-fold dilution with distilled water, the sol had the following properties:
$\lambda^A$max = 416 nm
$A_{416\ nm}^{1\ cm} = 1.12$
pH = 7.0

4.2. Preparation of Testosterone-11α-hemisuccinate-BSA 40 mg testosterone-11α-hemisuccinate is dissolved in 2 ml dimethyl-formamide and the solution is cooled to −15° C. 140 mg bovine serum albumin is dissolved in 3 ml distilled water, after which 1 drop 4 N NaOH and 2 ml DMF are added, and the whole is cooled to −15° C.

12.5 μl N-methylmorpholine and 12.5 μl isobutyl chloroformate are now added to the steroid solution. After 3 minutes, the solution is added to the BSA solution. After stirring for 1 hour at −15° C. and 3 hours at 0° C., the solution is transferred to a dialysis bag and dialysed overnight against running tap water. The dialysate is passed through a Sephadex G25 column, optionally after centrifugation, and the protein fraction is collected and freeze-dried.

4.3. Preparation of Antisera for Testosterone

Rabbits were immunized by injection of 1.25 mg testosterone-11α-hemisuccinyl-BSA, dissolved in 2.5 ml physiological saline, and 2.5 ml complete Freunds adjuvant (1 ml i.m. 3×, interval 1 week). They were then given an i.v. injection of 1 ml of a solution of 1.25 mg testosterone-11α-hemisuccinyl-BSA in 5 ml physiological saline.

This injection scheme was repeated until the titre of the antiserum was sufficiently high. The rabbits were then bled out, and the sera were stored at −20° C. until use.

4.4. Preparation of Polystyrene Tubes Coated With Rabbit Immunoglobulin Against Testosterone A rabbit anti-testosterone immunoglobulin solution is made by salting out with 180 g/l Na$_2$SO$_4$ as described in example I point 2.

The dialysed immunoglobulin solution is diluted (to a concentration of 1 μg immunoglobulin/ml) with a buffer consisting of 0.1 mol/liter NaH$_2$PO$_4$.H$_2$O, 60 g/l sucrose, adjusted to pH 7.4 with 4 mol/l NaOH. 1 ml of the immunoglobulin solution is pipetted into each 3 ml polystyrene tube, and incubated overnight at room temperature. The tubes are then emptied by suction and filled with 1 ml 10 g/l BSA solution in the above-noted buffer. After two hours, the tubes are emptied by suction and washed 3× with 3 ml distilled water. The tubes are dried completely by suction and are further dried over silica gel overnight. They are then packed in aluminium foil in sets of 25 with a bag of silica gel and stored at 4° C.

4.5. Preparation of Silver Particle-Testosterone-11α-Hemisuccinyl-BSA Conjugate 20 ml of the silver sol, prepared as described in 4.1., was diluted with 80 ml 0.3 g/l NaCl and the pH was adjusted to 7.0 with 0.01 mol/liter NaOH solution in distilled water. $A_{421\ nm}^{1\ cm} = 1.08$.

3 ml of a solution of testosterone-11α-hemisuccinyl-BSA, 175 μg/ml in 0.3 g/l NaCl adjusted to pH 7.0 with 0.01 mol/l NaOH, is then added dropwise to 15 ml of this sol with vigorous stirring by a magnetic stirrer.

The whole is incubated for about 10 minutes, after which 2 ml 10 g/l Carbowax 20 M solution in 0.3 g/l NaCl, adjusted to pH 7.0 with 0.01 mol/l NaOH, is added. The crude conjugate is subsequently washed by centrifuging 10 ml at 25000 N/kg for 20 minutes. 9 ml supernatant is now removed by suction and replaced by 9 ml washing liquid consisting of 1 g/l Carbowax 20 M solution in 0.3 g/l NaCl, adjusted to pH 7.0 with 0.01 mol/liter NaOH dissolved in distilled water. After washing 3 times, the conjugate is again centrifuged after which the supernatant liquid is removed by suction. The residue is redispersed in 0.02 mol/liter phosphate buffer, pH 7.4. The conjugate solution now has a pH of 7.4 and $A_{421\ nm}^{1\ cm} = 1.08$. The washed conjugates are stored at 4° C. until use.

4.6. Test Protocol for the Determination of Testosterone with the Silver Particle Testosterone-11α-Hemisuccinyl-BSA Conjugate 1. Pipette a 1 ml sample into a polystyrene tube coated with rabbit anti-testosterone immunoglobulin and incubate for 2 hours at room temperature.

2. Empty the tube by suction and wash 3× with 2 ml 0.02 mol/liter phosphate buffer, pH 7.0.

3. Pipette 1 ml of the silver particle testosterone-11α-hemisuccinyl-BSA conjugate, $A_{421\ cm}^{1\ cm} = 1.08$, into the tube and incubate for 16 hours.

4. Now suck the tube empty and wash with 2 ml 0.02 mol/liter phosphate buffer, pH 7.0.

5. Pipette 1 ml 0.1 mol/liter HCl, solution in distilled water, into the tubes and allow this to act for 30 minutes.

6. Measure the liquid in the tube $A_{421\ nm}^{1\ cm}$.

4.7. Results

The test media were colourimetrically determined with the aid of a standard curve, whereby amounts of testosterone of the magnitude of 0.5 ng/ml and greater could be determined.

EXAMPLE V

Determination of the Titer of Human Anti-Rubella Sera

5.1. Preparation of the Rubella Antigen 200 ml of a host cell suspension (BKH 21C3 from the Rijks Instituut voor Volksgezondheid, RIV) in culture medium (concentration 10$^5$ live cells per ml) is introduced into a roller bottle (surface 490 cm$^2$). The cell culture is kept for 16 to 20 hours at 37° C. The culture medium is then removed and the cell layer is washed twice with 20 ml phosphatebuffered saline solution (PBS). 10 ml virus suspension (virus type M33 RIV) is then diluted 1:100 with PBS and introduced into the bottle, after which the whole is incubated at 37° C. for about 2½ hours.

100 ml maintenance medium is now added and the culture is then kept at 37° C. After a period of at least 64 hours, but not exceeding 136 hours, depending on the assessment of the cytopathic effect, the incubated monolayer of infected cells is harvested. The maintenance medium is removed, and the monolayer of cells is washed once with 20 ml PBS. The cells are loosened from the wall by means of sterile glass beads, taken up in 90 ml PBS and frozen at −20° C.

After thawing, 10 ml glycine solution (1 mol/l), the pH being adjusted to 9.0 with solid NaOH, is added to 90 ml cell suspension, and the whole is thoroughly mixed for 6 hours at 37° C. The cell suspension is now ultrasonicated for 30 minutes, with cooling in ice, and subsequently centrifuged at 30000 N/kg for 30 minutes at 4° C. The supernatant containing the Rubella virus is collected and inactivated by consecutive addition of:

1:100 (v/v) NaOH (1 mol/liter) solution in distilled water

1:100 (v/v) freshly prepared 10% β-propiolactone solution in distilled water.

The liquid is allowed to stand for 48 hours at 4° C., after which it is centrifuged for 30 minutes at 30000 N/kg and 4° C.

The supernatant is the liquid containing the Rubella virus, which can if necessary be stored at −20° C. until use.

5.2. Coating of Microelisa$^{(R)}$ Plates with Rubella Antigens

The Rubella antigen solution, prepared as described in 5.1., is diluted 1:100 with a 0.05 mol/liter carbonate buffer, pH 9.6. 100 μl of this liquid Rubella antigen solution is pipetted into each well of the Microelisa plate and the whole is subsequently incubated for 16 hours at 4° C. The well of the Microelisa$^{(R)}$ plate are now emptied by suction and washed 3 times with 300 μl 0.05 mol/l phosphate buffer, ph 7.4, to which 9 g/l NaCl and 0.5 g/l Tween 20 have been added.

5.3. Preparation of Sheep Anti-Human Immunoglobulin Solution

Normal human serum is salted out with 140 g/l $Na_2SO_4$, which is added as a solid in small portions. After standing for 1 hour at room temperature, the turbid liquid is centrifuged at 25000 N/kg for 10 minutes. The supernatant is removed by suction, after which the residue is washed with a 140 g/l $Na_2SO_4$ solution in distilled water. After centrifuging and removal of the supernatant by suction, the residue is dissolved in 9 g/l NaCl, after which the immunoglobulin solution is dialysed for 48 hours against 9 g/l NaCl at 4° C. The immunoglobulin content is then determined by the $A_{260}{}^{1\ cm}$, $A_{280}{}^{1\ cm}$ method.

Sheep were immunized with a diluted solution of this human immunoglobulin solution according to the following scheme.:

day 1

0.5 mg human immunoglobulin dissolved in 0.5 ml physiological saline, to which 0.5 ml complete Freunds adjuvant has been added.

Injection: intramuscular.

day 14

1.0 mg human immunoglobulin dissolved in 0.5 ml physiological saline, to which 0.5 ml incomplete Freunds adjuvant has been added.

Injection: intramuscular.

day 28

2.0 mg human immunoglobulin dissolved in 0.5 ml physiological saline, to which incomplete Freunds adjuvant has been added.

Injection: intramuscular.

day 42

1.0 mg human immunoglobulin dissolved in 1.0 ml physiological saline.

Injection: intravenous.

day 56

Sampling of blood.

The immunoglobulin fractions were obtained from the sheep anti-human immunoglobulin sera by salting out according to the above-described 140 g/l $Na_2SO_4$ method. After washing for the third time, the residue was dissolved in 9 g/l NaCl, after which the immunoglobulin solution was dialysed against a 0.3 g/l NaCl solution in distilled water, adjusted to pH 7.0 with 0.2 mol/l $K_2CO_3$ dissolved in distilled water.

After centrifuging this dialysed sheep anti-human immunoglobulin solution at 160000 N/kg for 15 minutes, the immunoglobulin content was determined by the $A_{260\ nm}{}^{1\ cm}$, $A_{280\ nm}{}^{1\ cm}$ method.

5.4. Preparation of the Gold-Particle Sheep Anti-Human Immunoglobulin Conjugate

The gold sol was prepared by the method described in 1.1. and the conjugate was prepared in a way analogous to the method described in 1.4. whereby in this case the sheep immunoglobulin solution prepared in 5.3. was used, with an immunoglobulin content of 125 μg per ml.

5.5. Test Protocol

The sample of human sera is diluted 1:25 with 0.2 mol/l Trometamol/HCl/NaCl buffer, pH 7.4, to which 0.5 g/l Tween 20 has been added.

1. 100 μl of diluted human serum is pipetted into each well and the whole is incubated for 30 minutes at room temperature.

2. The well is emptied by suction and washed 3 times with 300 μl 0.2 mol/l Trometamol/HCl/NaCl buffer, pH 7.4, to which 0.5 g/l Tween 20 has been added.

3. 100 μl gold particle sheep anti-human immunoglobulin conjugate ($A_{536\ nm}{}^{1\ cm}=1.00$) is now pipetted into the well and the whole is incubated for 16 hours at room temperature.

4. The well is emptied by suction and washed 3 times with 300 μl 0.01 mol/l Trometamol/HCl/NaCl buffer, pH 7.4, to which 0.5 g/l Tween 20 has been added.

5. Pipette 100 μl 0.1 mol/l HCl dissolved in distilled water into the well and allow this to act for 30 minutes while shaking.

6. After this, measure the light absorption at 536 nm, using a small volume spectrophotometer.

5.6. Results

An $A_{536\ nm}{}^{1\ cm}$ of about 0.230 was measured for sera with an HAI titer of 512, while a reasonable linear correlation was further found between the HAI titres of the human sera investigated and the $A_{536\ nm}{}^{1\ cm}$—values obtained in the above-mentioned test.

EXAMPLE VI

Determination of HCG with the aid of an iron oxide anti-HCG conjugate.

6.1. Preparation of the Iron Oxide Sol

A solution consisting of 9 mmol/l $FeCL_3$ and 1 mmol/l HCl is heated to a temperature of 95° C. during 65 hours. The initially slightly yellow solution discolors to orange-red due to the formation of iron oxide sol particles. The iron oxide sol obtained in this way consists of cubic iron oxide particles with an edge between 40 and 80 nm as verified by electron microscopy. A local light-absorption maximum is found at 370 nm. A sol with an iron oxide content of 0.45 mmol/l exhibits an $A_{370\ nm}^{1\ cm} = 1.0$ and a pH of 2.7 just after the preparation.

6.2. Preparation of the Iron Oxide Anti-HCG Conjugate

Rabbit anti-HCG sera were prepared according to a method analogous to that described for anti-HPL sera in example 1.2.

The immunoglobulin fraction hereof was obtained by adding $Na_2SO_4$, separating the residue, redispersing the latter in a 180 g/l $Na_2SO_4$ solution and dialysing this dispersion against a solution containing 5 mmol/l NaCl. The immunoglobulin content was determined as described in example 1.3.

The iron oxide sol of 5.1 was diluted, resulting in an iron oxide content of 0.45 mmol/l. To 25 ml hereof, 0.5 ml glutaraldehyde 250 g/l was added and the mixture was incubated during 30 minutes at room temperature and pH 2.8. Subsequently, 0.63 ml rabbit anti-HCG immunoglobulin solution, containing 640 µg/ml immunoglobulin, was added.

After an incubation of 1 hour at room temperature and pH 2.7 the pH of the mixture was adjusted to 7.0 with a NaOH solution and the incubation of the mixture was continued overnight at 0°-4° C.

Before use, the conjugates were washed by centrifuging, sucking off the supernatant and resuspending in a buffer consisting of 0.1 mol/l Tris/NaCl/HCl (pH=7,4), 1 g/l BSA and 0.2 g/l Carbowax 20 M. Finally, the volume of the sol was adjusted, so that $A_{370\ nm}^{1\ cm} = 1.0$.

6.3. Coating of Microelisa(R) Plates with Rabbit Anti-HCG Immunoglobulins

Microelisa(R) plates were coated with rabbit anti-HCG immunoglobulin as described for coating with anti-HPL immunoglobulins in example 1.5.

6.4. Test Protocol for HCG Determination with Iron Oxide Anti-HCG Conjugates A dose response curve was made for HCG, that is solved in a mixture of 0.04 mol/l phosphate buffer, 1 g/l BSA and 9 g/l NaCl (pH=7.4), according to the following test protocol.

1. Pipette 0.1 ml of the standard HCG solution into a well of a Microelisa(R) plate, coated with anti-HCG and incubate for 2.5 hours at 37° C.
2. Suck the well empty.
3. Pipette 0.1 ml iron oxide anti-HCG ($A_{370\ nm}^{1\ cm} = 1.0$) into the well and incubate during the night at 37° C.
4. Empty the well by suction and wash it 8 times with 0.3 ml of a solution containing 0.1 mol/l Tris/HCl/NaCl buffer (pH=7.4) and 0.5 g/l Tween 20.
5. Pipette 0.1 ml of a solution containing 0.1 mol/l NaOH and allow this to act for 15 minutes.
6. Measure the light absorption at 360 nm with a small volume spectrophotometer.

The results of a dose response curve are given in the table below.

| HCG concentration in the standard solution, in mIU/ml | $A_{360\ nm}^{1\ cm}$ |
|---|---|
| 2000 | 0.367 |
| 1000 | 0.429 |
| 500 | 0.414 |
| 250 | 0.304 |
| 125 | 0.275 |
| 63 | 0.205 |
| 31 | 0.179 |
| 16 | 0.172 |
| 8 | 0.154 |
| 4 | 0.142 |
| 0 | 0.096 |

6.5. Determination of HCG in the urine of pregnant women

The urines of pregnant women were diluted such that the HCG level lay in the range 1–500 mIU HCG/ml. With the aid of the test protocol of 5.4. the HCG concentration of the diluted samples were determined using the standard curve constructed.

EXAMPLE VII

Determination of HCG with the aid of gold particle anti-HCG conjugate in an agglutination test.

7.1. Preparation of Reagents

A gold sol is prepared according to the method described in 1.1. and rabbit anti-HCG sera and immunoglobulin fractions hereof as described in 5.2.

A gold particle anti-HCG conjugate is prepared with the gold sol and the rabbit anti-HCG solutions according to the method described in 1.4.

7.2. Test Protocol

1. Pipette 1 ml of the gold particle anti-HCG conjugate ($A_{540\ nm}^{1\ cm} = 1.50$) into a test tube of approximately 3 ml.
2. Pipette herein 0.1 ml of the urine to be tested and mix.
3. Judge the color of the conjugate after an incubation of 1 hour at room temperature:

a color change from red to colourless indicates that the sample is strongly positive a color change from red to purple indicates that the sample is positive and contains 1 IU HCG/ml or more if the color does not change the sample is negative, i.e. it contains 0.4 IU HCG/ml or less.

7.3. Results

With the aid of the test protocol of 7.2. it is possible to diagnose pregnancy on the 33–35th day after the last menstruation.

EXAMPLE VIII

Competitive Receptor Assay for HCG

8.1. Preparation of Purified HCG Receptor Protein From Bovine Corpora Lutea (BCL)

HCG receptor protein from BCL was prepared by the method described in detail by Khan and Saxena in Enzyme Labelled Immunoassay of Hormones and Drugs ed. S.B. Pal, Publ. Walter de Gruyter, Berlin, New York 1978. Fresh BCL tissue was pulverized, homogenized, filtered, further homogenized and centrifuged at 6500 N/kg. The supernate was centrifuged at 130,000 N/kg, the obtained pellet homogenized and centrifuged in a zonal rotor with a sucrose gradient and eluted. The freeze dried fractions containing the HCG receptor membranes were redissolved and after centrifugation Mannitol was added to the clear supernate, whereafter the pH was adjusted to 7.0. The obtained dispersion was purified by affinity chromatography on CNBr-activated sepharose 4B coupled with human LH. After elution of the bound receptor, the pH was immediately adjusted to 7 and Triton X-100 was removed by adsorption on Bio-beads. The obtained dispersion of HCG receptor protein was thoroughly dialyzed against PBS, pH 7.0 and stored at 4° C.

8.2. Coating of Polystyrene Micro Titration Plates with HCG Receptor Protein To this end a HCG receptor protein receptor solution is prepared with a content of 25 μg protein/ml by diluting the HCG receptor protein in PBS with a solution of 0.04 mol/l $Na_2HPO_4$, adjusted to a pH of 7.4 with a solution of 0.04 mol/l $NaH_2PO_4$ to which 0.1 g/l Merthiolate is added. Micro titration plates were coated with this HCG receptor solution according to the protocol described in 1.5.

8.3. Preparation of a Gold Dispersion

A gold dispersion consisting of particles having a diameter between 6 and 15 nm was prepared by adding 14 ml of a solution containing 10 g/l sodium citrate $2H_2O$ to a boiling solution containing 100 mg/l chloroauric acid ($HAuCl_4$), and the mixture is kept boiling for 15 minutes. The obtained orange red gold dispersion is cooled down to room temperature and re-adjusted to a volume of 500 ml in a volumetric flask. The gold dispersion had a light absorption maximum at 523 nm and $A_{523\ nm}^{1\ cm} = 1.0$.

8.4. Preparation of a Gold Particle HCG Conjugate

A solution containing 5 mg purified HCG/ml in PBS (pH=7.0) was thoroughly dialyzed against a solution containing 5 mmol/l NaCl, adjusted to a pH of 4,5 by means of HCl. 1 ml of the dialyzed HCG solution was added to 500 ml of the gold dispersion and stirred for 10 minutes at room temperature. 10 ml of a solution containing 10 g Carbowax 20 M/l was added to the fresh conjugate and incubated for another 10 minutes. Thereafter the pH was adjusted to 7.4 by means of a $K_2CO_3$ solution. The conjugate was stored at 4° C. Just before use 1 ml of a 1 mol/l TRIS/HCl/NaCl buffer (pH=7.4) containing 1 g/l BSA was added to 10 ml of the stored conjugate dispersion.

8.5. Test Protocol for a Competitive HCG Assay

100 μl of a standard HCG solution (or the sample) was added to a well of micro titration plates coated with HCG receptor protein and incubated for one hour at room temperature. Thereafter 100 μl of the buffered gold particle HCG conjugate was added and incubated for four hours at room temperature. The well was emptied and washed with 0.3 ml 0.01 mol/l TRIS/HCl-/NaCl buffer pH=7.4.

Finally 0.1 ml 0.1 mol/l NaOH solution in water was added and incubated for 10 minutes. The light absorption of the fluid in a well was measured at 536 nm using a small volume spectrophotometer.

8.6. Result

A dose-response curve for free HCG was obtained in a HCG concentration range between 0 and 1000 mIU/ml having a midpoint near 100 mIU HCG/ml. The detection limit was about 10 mIU HCG/ml. The HCG concentration measured in samples was usually higher than determined with an EIA.

EXAMPLE IX

Sandwich Assay for HCG Using an Insolubilized HCG Receptor and a Gold Particle-Anti HCG Conjugate For this assay microtitration plates were coated with HCG receptor protein as described in Example 8.2. A gold particle-anti HCG conjugate was prepared as described in Example 1.4. using rabbit anti-HCG in stead of rabbit anti-HPL.

9.1. Test Protocol 0.1 ml of a standard solution HCG in 0.1 mol/l TRIS/HCl/NaCl buffer pH=7.4 containing 1 g/l BSA (or sample) is pipetted into a well of the microtitration plate coated with HCG receptor protein and incubated for 1 hour at room temperature. Then the wells are emptied and 0.1 ml of the gold particle anti HCG conjugate is pipetted into each well and incubated overnight at room temperature. The wells are emptied and washed 6 times with 0.3 ml 0.01 mol/l TRIS/HCl/NaCl buffer pH=7.4.

0.1 ml and 0.1 mol/l NaOH is pipetted into each well and incubated for 15 minutes. The light absorption at 536 nm of the content of the wells is measured using a small volume spectrophotometer.

9.2. Test Results

Dose response curves were obtained for HCG concentration between 0 and 1000 mIU/ml. The detection limit was about 5 mIU/ml. HCG concentrations measured in samples were about the same as measured with EIA.

I claim:

1. The process for the detection and/or determination of one or more components of the reaction between a specific binding protein and the corresponding bindable substance in an aqueous test sample, by applying the known binding affinity of such components for one another, comprising:
(a) employing one or more labelled components, obtained by coupling directly or indirectly the desired component of said reaction to particles of an aqueous sol dispersion of a metal, metal compound or polymer nuclei coated with a metal or metal compound, having a particle size of at least 5 nm, and
(b) detecting and/or determining during the reaction or after an adequate reaction time and optionally after separation of the bound and free labelled components, the physical properties and/or the amount of the metal and/or a formed agglomerate containing said sol dispersed particles in the test sample or one of the derived fractions, which detection and/or determination provides a qualitative and/or quantitative indication of the component or components to be detected and/or determined.

2. The process according to claim 1, whereby the component or components of the reaction between a specific binding protein and the corresponding bindable substance are immunochemical components, such as haptens, antigens, or antibodies, comprising:
(a) employing labelled components, obtained by coupling directly or indirectly the desired immuno chemical component to particles of an aqueous sol dispersion of a metal, metal compound or polymer nuclei coated with a metal or metal compound, having a particle size of at least 5 nm, and
(b) detecting or determining after an adequate reaction time and optionally after separation of the bound and free labelled components, the physical properties and/or the amount of the metal and/or a formed agglomerate containing said metal particles in the test sample or one of the derived fractions, which detection and/or determination provides a qualitative and/or quantitative indication of the immunological component or components to be detected and/or determined.

3. The process according to claim 1, wherein one or more labelled components are used, obtained by coupling directly or indirectly the desired reactant to particles of a sol, having a particle size varying from 10 to 100 nm.

4. The process according to claim 1, wherein the labelled component is obtained by adding to a sol of a metal, a metal compound or polymer nuclei coated with a metal or metal compound, a certain amount of the immunochemical component to be labelled, which latter component completely or partially coats the sol particles, after which further coating may be carried out with an immunochemically inert polar macromolecule.

5. The process according to claim 1, wherein the labelled component is obtained by adding to a sol of a metal, a metal compound or polymer nuclei coated with a metal or a metal compound, one or more immunochemically inert hydrophilic macromolecules which coat the sol particles, after which the immunochemical component is coupled to the coating material.

6. The process according to claim 1, wherein the labelled component is obtained by:
(a) introducing a metal sol into an environment of monomers, causing said monomers to polymerize or copolymerize in situ, so that coating of the sol particles results, and
(b) subsequently coupling the immunochemical component to the polymeric material.

7. The process according to claim 1, wherein the sol particles are first protected by an inert hydrophilic macromolecule, after which (co)-polymerization occurs under the influence of an inorganic initiator.

8. The process according to claim 1, wherein the dispersed particles are of a sol of gold, silver or platinum, or compounds of these metals, or iron or copper compounds.

9. The process according to claim 1, wherein after separation of the bound and the free labelled components, the physical properties and/or the amount of the metal is determined in the fraction containing the bound labelled component.

10. The process according to claim 1, wherein the immunochemical component or components to be determined is/are allowed to react with one or more insolubilized immunochemical component(s), before the labelled component or components is/are added.

11. The process according to claim 1, wherein the bound labelled component or components is/are disengaged after separation of the free labelled component or components and the amount of the metal or metals is/are determined in the obtained liquid fraction.

12. The process according to claim 1, wherein two or more immunochemical components are determined in one test sample by use of two or more different labelled components.

13. The process according to claim 1, wherein the occurrance of a change in color or color intensity of the reaction mixture is observed or measured, which change is a qualitative or quantitative indication of the immunochemical component to be determined.

14. A test kit, to be used for the detection and/or determination of one or more components of the reaction between a specific binding protein and a corresponding bindable substance thereto in an aqueous medium according to a predetermined protocol, comprising:
(a) a metal-labelled component which has been obtained by coupling a component of said reaction to particles of an aqueous sol dispersion of a metal, metal compound or polymer nuclei coated with a metal or metal compound, which parties have a size of at least 5 nm;
(b) one or more additional immunochemical reagents of which at least one reagent is a ligand or an immobilized ligand, which ligand is selected from the group consisting of
  (aa) a ligand capable of binding with the metal-labelled component (a);
  (bb) a ligand capable of binding with a binding partner of the metal-labelled component (a);
  (cc) a ligand capable of binding with at least one of the component(s) to be determined; and
  (dd) a ligand capable of binding with at least one of the binding partners of at least one of the component(s) to be determined; and
(c) directions for the performance of a protocol for the detection and/or determination of one or more components of an immunochemical reaction in an aqueous medium between a specific binding protein and a corresponding bindable substance thereto.

15. A test kit according to claim 14, in which the aqueous dispersion is a sol, having particles with a size varying from 10–100 nm, which are either directly coated by the component of said reaction or by an inert polymer, to which the desired component has been coupled.

16. The test kit according to claim 14, of which the labelled component is an immuno component.

17. The test kit according to claim 14, of which the labelled component is freeze-dried.

18. The test kit according to claim 17, of which the freeze-dried reagent contains also a buffer substance.

19. Test kit according to claim 14, in which the dispersion is a gold, silver, or iron oxide sol.

20. Test kit according to claim 19, in which the particles range from 10–100 nm in size.

21. Test kit according to claim 14 also containing an insolubilized immunocomponent, in which the immunocomponent is selected from the group consisting of (1) a component immunochemically similar to the component to be determined, or (2) a binding partner of the component to be determined.

22. Test kit according to claim 21, in which said reagent containing metal dispersed particles is freeze-dried.

23. Test kit according to claim 22, in which a buffer is included with said reagent.

24. A method for the determination of a first component of an immunochemical reaction in an aqueous medium selected from the group consisting of a specific binding protein and its corresponding bindable substance, comprising:
(a) contacting a sample containing the first component to be determined with (1) a known amount of a reagent consisting essentially of metal sol dispersion particles having a particle size of at least 5 nm, which particles have attached to their surfaces an immunochemical component which is immunochemically equivalent to said first component to be determined, and (2) a known amount of an insolubilized second component capable of reacting with either said first component to be determined or said reagent;
(b) allowing sufficient time for reaction to take place, whereby (1) a fraction of said first component to be determined bound to said insolubilized component, and (2) a fraction of said first component to be determined free from said insolubilized component are produced; and
(c) determining the amount of the metal of the metal sol dispersion particles in one of said fractions, which is a measure of the amount of said first component to be determined in said sample.

25. A method for the determination of a first component of an immunochemical reaction in an aqueous medium, selected from the group consisting of a specific binding protein and its corresponding bindable substance, comprising:
(a) contacting a sample containing the first component to be determined with (1) a known amount of a reagent consisting essentially of metal sol dispersion particles having a particle size of at least 5 nm, which particles have attached to their surfaces (i) an immunochemical component immunochemically equivalent to said first component to be determined, and (ii) an immunochemically inert macromolecule, and (2) a known amount of an insolubilized second immunochemical component capable of reacting with either said first component to be determined or said reagent;
(b) allowing sufficient time for reaction to take place, whereby (1) a fraction of said first component to be determined bound to said insolubilized component and (2) a fraction of said first component to be determined free from said insolubilized component are produced; and
(c) determining the amount of the metal of the metal sol dispersion particles in one of said fractions, which is a measure of the amount of said first component to be determined in said sample.

26. A method for the determination of a first component of an immunochemical reaction in an aqueous medium, selected from the group consisting of a specific binding protein and its corresponding bindable substance, comprising:
(a) contacting a sample containing the first component to be determined with (1) a known amount of a reagent consisting essentially of metal sol dispersion particles having a particle size of at least 5 nm, which particles have a coating of an inert hydrophilic polymer or copolymer, the surface of each coated particle having attached to it an immunochemical component which is immunochemically equivalent to said first component, and (2) a known amount of an insolubilized second immunochemical component capable of reacting with either said first component to be determined or said reagent;
(b) allowing sufficient time for reaction to take place, whereby (1) a fraction of said first component to be determined bound to said insolubilized component and (2) a fraction of said first component to be determined free from said insolubilized component are produced; and
(c) determining the amount of the metal of the metal sol dispersion particles in one of said fractions, which is a measure of the amount of said first component to be determined in said sample.

27. A method for the determination of a first component of an immunochemical reaction in an aqueous medium, selected from the group consisting of a specific binding protein and its corresponding bindable substance, comprising:
(a) contacting a sample containing the first component to be determined with (1) a known amount of reagent consisting essentially of metal sol dispersion having a particle size of at least 5 nm, which sol particles have attached to their surfaces a second immunochemical component of said reaction capable of reacting with said first component to be determined, and (2) a known amount of an insolubilized second immunochemical component which is immunochemically equivalent to said first component and capable of reacting with said reagent;
(b) allowing sufficient time for reaction to take place, whereby (1) a fraction of said first component to be determined bound to said insolubilized component and (2) a fraction of said first component to be determined free from said insolubilized component are produced; and
(c) determining the amount of the metal of the metal sol dispersion particles in one of said fractions, which is a measure of the amount of said first component to be determined in said sample.

28. A method for the determination of a first component of an immunochemical reaction in an aqueous medium, selected from the group consisting of a specific binding protein and its corresponding bindable substance, comprising:
(a) contacting a sample containing the first component to be determined with (1) a known amount of a reagent, said reagent consisting essentially of metal sol dispersion particles having sizes of at least 5 nm, which sol particles have attached to their surfaces (i) a second immunochemical component capable of reacting with said first component to be determined, and (ii) an immunochemically inert macromolecule, and (2) a known amount of an insolubilized second immunochemical component which is immunochemically equivalent to said first component to be determined and capable of reacting with said reagent;
(b) allowing sufficient time for the reaction to take place, whereby (1) a fraction of said first component to be determined bound to said insolubilized component and (2) a fraction of said first component to be determined free from said insolubilized component are produced; and
(c) determining the amount of the metal of the metal sol dispersion particles in one of said fractions, which is a measure of the amount of said first component to be determined in said sample.

29. A method for the determination of a first component of an immunochemical reaction in an aqueous medium, selected from the group consisting of a specific binding protein and its corresponding bindable substance, comprising:
(a) contacting a sample containing the first component to be determined with (1) a known amount of a reagent consisting essentially of metal sol dispersion particles having a particle size of at least 5 nm, which particles have a coating of an inert hydrophilic polymer or co-polymer, the surface of each coated sol particle having attached to it a second immunochemical component of said reaction capable of reacting with said first component to be determined, and (2) a known amount of an insolubilized third immunochemical component which is immunochemically equivalent to said first component and capable of reacting with said reagent;
(b) allowing sufficient time for the reaction to take place, whereby a fraction of said first component to be determined bound to said insolubilized component and a fraction of said first component to be determined free from said insolubilized component are produced; and
(c) determining the amount of the metal of the metal sol dispersion particles in one of said fractions, which is a measure of the amount of said first component to be determined in said sample.

30. A method for the determination of a first component of an immunochemical reaction in an aqueous medium, selected from the group consisting of its corresponding bindable substance, comprising:
(a) binding an amount of a second immunochemical component of said reaction capable of reacting with said first component to be determined, to the surface of a water-insoluble, water-insuspensible, solid carrier;
(b) contacting said bound second component with a sample containing the first component to be determined;
(c) allowing sufficient time for reaction to take place;
(d) contacting said bound reaction product of (c) with a known amount of a reagent consisting essentially of metal dispersion sol particles having a particle size of at least 5 nm, which sol particles have attached to their surface an immunochemical component capable of reacting with said first component to be determined;
(e) allowing sufficient time for reaction to take place, to bind a fraction of said reagent to that part of said bound second immunochemical component which has undergone the reaction in step (c), leaving a remaining fraction of said reagent free and not bound; and
(f) determining the amount of the metal sol dispersion particles in the free reagent fraction or the bound reagent fraction, which is a measure of the amount of said first component to be determined in said sample.

31. A method for the determination of a first component of an immunochemical reaction in an aqueous medium, selected from the group consisting of a specific binding protein and its corresponding bindable substance, comprising:
(a) binding an amount of a second immunochemical component capable of reacting with said first component to be determined, to the surface of a water-insoluble, water-insuspensible, solid carrier;
(b) contacting said bound second component with a sample containing the first component to be determined;
(c) allowing sufficient time for reaction to take place;
(d) contacting said bound reaction product of (c) with a known amount of reagent consisting essentially of metal sol dispersion particles, having a particle size of at least 5 nm, said sol particles having attached to their surfaces (i) an immunochemical component capable of reacting with said first component to be determined, and (ii) an immunochemically inert macromolecule;
(e) allowing sufficient time for reaction to take place to bind a fraction of said reagent to that part of said bound second component which has undergone the reaction in step (c), leaving a remaining fraction of said reagent free and not bound; and
(f) determining the amount of the metal sol dispersion particles in the free reagent fraction or the bound reagent fraction, which is a measure of the amount of said component to be determined in said sample.

32. A method for the determination of a first component of an immunochemical reaction in an aqueous medium, selected from the group consisting of a specific binding protein and its corresponding bindable substance, comprising:
(a) binding an amount of a second immunochemical component capable of reacting with said first component to be determined, to the surface of a water-insoluble, water-insuspensible, solid carrier;
(b) contacting said bound second component with a sample containing the first component to be determined;
(c) allowing sufficient time for reaction to take place;
(d) contacting said bound reaction product of (c) with a known amount of reagent consisting essentially of metal sol dispersion particles, having a particle size of at least 5 nm and having a coating of an inert hydrophilic polymer of co-polymer, the surface of each coated particle having attached to it an immunochemical component capable of reacting with said first component to be determined;
(e) allowing sufficient time for reaction to take place to bind a fraction of said reagent to that part of said bound second component which has undergone the reaction in step (c), leaving a remaining fraction of said reagent free and not bound; and
(f) determining the amount of the metal sol dispersion particles in the free reagent fraction or the bound reagent fraction, which is a measure of the amount of said first component to be determined in said sample.

33. A method for the determination of a first component of an immunochemical reaction in an aqueous medium, selected from the group consisting of a specific binding protein and its corresponding bindable substance, comprising:
(a) contacting a sample containing the first component to be determined with a known amount of a reagent, said reagent consisting essentially of metal sol dispersion particles having a particle size of at least 5 nm, said sol particles having attached to their surfaces a second immunochemical component of said reaction capable of reacting with said first component to be determined;
(b) allowing sufficient time for reaction to take place; and (c) determining the color of the reaction solution, which is a measure of the amount of said first component to be determined in said sample.

34. A method for the determination of a first component of an immunochemical reaction in an aqueous medium, selected from the group consisting of a specific binding protein and its corresponding bindable substance, comprising:
(a) contacting a sample containing the first component to be determined with a known amount of a reagent consisting essentially of metal sol dispersion particles having a particle size of at least 5 nm, said sol particles having attached to their surfaces (i) a second immunochemical component of said reaction capable of reacting with said first component to be determined, and (ii) an immunochemically inert macromolecule;
(b) allowing sufficient time for a reaction to take place; and
(c) determining the color of the reaction solution, which is a measure of the amount of said first component to be determined in said sample.

35. A method for the determination of a first component of an immunochemical reaction in an aqueous test medium selected from the group consisting of a specific binding protein and its corresponding bindable substance, comprising:
(a) contacting a sample containing the first component to be determined with a known amount of a reagent consisting of metal sol dispersion particles having a particle size of at least 5 nm, said sol particles having a coating of an inert hydrophilic polymer or copolymer, the surface of each coated particle having attached to it a second immunochemical component of said reaction capable of reacting with said first component to be determined;
(b) allowing sufficient time for a reaction to take place; and
(c) determining the color of the reaction solution, which is a measure of the amount of said first component to be determined in said sample.

36. A method for the immunochemical determination of human placental lactogen (HPL), comprising:
(a) binding a known amount of rabbit anti-HPL immunoglobulin to the surface of a water-insoluble, water-insuspensible solid carrier;
(b) contacting said bound immunoglobulin with a sample solution containing the HPL to be determined;
(c) allowing sufficient time for an immunological reaction between the bound immunoglobulin and said HPL in the sample solution in step (b) to take place, to bind the HPL to be determined to the insolubilized rabbit anti-HPL, forming a first solid phase, and leaving a first liquid phase;
(d) separating the first liquid and solid phases;
(e) contacting said first reacted solid phase and bound HPL therein with a known amount of a reagent, said reagent consisting essentially of gold sol dispersion particles having a particle size of at least 5 nm, said particles having rabbit anti-HPL immunoglobulin attached to their surfaces;
(f) allowing sufficient time for a second immunological reaction to take place, to bind said reagent to that part of said HPL solid phase bound immunoglobulin which has undergone the reaction in step (c), to form a second solid phase and a second liquid phase;
(g) separating the second solid phase from the second liquid phase; and
(h) determining the amount of gold sol in the second liquid phase or the second solid phase, which is a measure of the amount of HPL in said sample solution.

37. A method for the immunochemical determination of hepatitis Surface B antigen (HBsAg), comprising:
(a) binding a known amount of sheep anti-HBsAg immunoglobulin to the surface of a water-insoluble, water-insuspensible solid carrier;
(b) contacting said bound immunoglobulin with a sample solution containing the HBsAg to be determined;
(c) allowing sufficient time for an immunological reaction between the bound immunoglobulin and the HBsAg in the sample solution in step (b) to take place, to bind the HBsAg to be determined to the insolubilized sheep anti-HBsAg, forming a first solid phase, and leaving a first liquid phase;
(d) separating the first liquid and solid phases;
(e) contacting said first reacted solid phase and bound HBsAg therein with a known amount of a reagent having a particle size of at least 5 nm, said reagent consisting essentially of gold sol particles, said sol particles having anti-HBsAg immunoglobulin attached to their surfaces;
(f) allowing sufficient time for a second immunochemical reaction to take place, to bind said reagent to that part of said HBsAg solid phase bound immunoglobulin which has undergone the reaction in step (c), to form a second solid phase and a second liquid phase;
(g) separating the second solid phase from the second liquid phase; and
(h) determining the amount of gold sol in the second liquid phase or the second solid phase, which is a measure of the amount of HBsAg in said sample solution.

38. A method for the immunochemical determination of testosterone in a liquid sample, comprising:
(a) binding a known amount of rabbit anti-testosterone immunoglobulin to the surface of a water-insoluble, water-insuspensible, solid carrier;
(b) contacting said bound rabbit anti-testosterone with a sample solution containing the testosterone to be determined;
(c) allowing sufficient time for an immunological reaction between the bound rabbit anti-testosterone immunoglubulin and the testosterone in the sample solution in step (b) to take place to bind the testosterone to be determined to the insolubilized rabbit anti-testosterone, forming a first solid phase, and leaving a first liquid phase;
(d) separating the first liquid and solid phases;
(e) contacting said first reacted solid phase and bound testosterone therein with a known amount of a reagent having a particle size of at least 5 nm, said reagent consisting essentially of silver sol dispersion particles, said sol particles having testosterone-11α-hemisuccinyl-bovine serum albumin attached to their surfaces, to form a silver particle-testosterone-11α-hemisuccinyl-bovine serum albumin conjugate;
(f) allowing sufficient time for a second immunochemical reaction to take place to bind said reagent to that part of said solid phase bound rabbit anti-testosterone immunoglobulin which has not undergone the reaction in step (c), to form a second solid phase and a second liquid phase;
(g) separating the second solid phase from the second liquid phase; and (h) determining the amount of silver sol in the second solid phase or the second liquid phase, which is a measure of the amount of testosterone in said liquid sample.

39. A method for the immunochemical determination of the titer of human anti-Rubella sera, comprising:
(a) binding a known amount of Rubella antigen to the surface of a water-insoluble, water-insuspensible, solid carrier;
(b) contacting said bound Rubella antigen with a human serum sample containing the titer of human anti-Rubella sera to be determined;
(c) allowing sufficient time for an immunological reaction between the bound Rubella antigen and the serum containing the titer of human anti-Rubella sera to be determined to take place to bind the anti-Rubella sera to the insolubilized Rubella antigen, forming a first solid phase, and leaving a first liquid phase;
(d) separating the first liquid and solid phases;
(e) contacting said first reacted solid phase and bound anti-Rubella titer therein with a known amount of a reagent, said reagent consisting essentially of gold sol dispersion particles having a particle size of at least 5 nm, said sol particles having sheep anti-human immunoglobulin attached to their surfaces to form a gold particle sheep antihuman immunoglobulin conjugate;
(f) allowing sufficient time for a second immunological reaction to take place to bind said reagent to the bound anti-Rubella titer solid phase, resulting in the binding of said reagent to that part of said bound antigen which has undergone the reaction in step (c), to form a second solid and a second liquid phase;
(g) separating the second liquid and solid phases; and
(h) determining the amount of gold sol in the second solid phase or the second liquid phase, which is a measure of the titer of the human anti-Rubella serum to be determined in said sample.

40. A method for the immunochemical determination of HCG, comprising:
(a) binding a known amount rabbit anti-HCG immunoglobulin to the surface of a water-insoluble, water-insuspensible solid carrier;
(b) contacting said bound rabbit anti-HCG immunoglobulin with a sample solution containing the HCG to be determined;
(c) allowing sufficient time for an immunological reaction between the rabbit anti-HCG immunoglobulin and and HCG in the sample solution in step (b) to take place, to bind the HCG to be determined to the insolubilized rabbit anti-HCG immunoglobulin, forming a first solid phase, and leaving a a first liquid phase;
(d) separating the first solid phase from the first liquid phase;
(e) contacting said first solid phase and bound HCG with a known amount of a reagent consisting essentially of iron oxide sol dispersion particles having a particle size of at least 5 nm, said particles having rabbit anti-HCG immunoglobulin attached to their surfaces;
(f) allowing sufficient time for a second immunological reaction to occur to bind said reagent to that part of said HCG solid phase bound immunoglobulin which has undergone the reaction in step (c), to form a second solid phase and a second liquid phase;
(g) separating the second solid and second liquid phases; and (h) determining the amount of iron sol in the second solid phase or the second liquid phase, which is a measure of the amount of the HCG to be determined in said sample solution.

41. A method for the immunochemical determination of HCG, comprising:
(a) contacting an aqueous sample containing the HCG to be determined with a known amount of a reagent consisting essentially of gold sol dispersion particles having a particle size of at least 5 nm, said sol particles having rabbit anti-HCG immunoglobulin attached to their surfaces;
(b) allowing sufficient time for an immunological reaction between said reagent and any HCG in the sample solution to take place; and
(c) determining the color of the sample solution, which is a measure of the amount of HCG to be determined in said sample solution.

42. A method for the determination of HCG, comprising:
(a) binding a known amount of HCG receptor protein to the surface of a water-insoluble, water-insuspensible solid carrier;
(b) contacting said bound receptor protein with a sample solution containing the HCG to be determined;
(c) allowing sufficient time for an immunological reaction between the insolubilized HCG receptor protein and the HCG to be determined;
(d) adding a known amount of reagent to said sample solution, said reagent consisting essentially of gold sol dispersion particles having a particle size of at least 5 nm and having HCG attached to their surfaces;
(e) allowing sufficient time for a reaction to take place between (1) the gold sol dispersion reagent and (2) the insolubilized HCG receptor protein not bound to HCG, to form a solid phase containing a fraction of gold sol dispersion reagent bound to insolubilized HCG receptor protein, and a liquid phase of unbound and free gold dispersion reagent;
(f) separating the liquid and solid phases; and
(g) determining the amount of gold sol in either the solid or liquid phase, which is a measure of the amount of HCG in said sample solution.

43. A method for the immunochemical determination of HCG, comprising:
(a) binding a known amount of HCG receptor protein to the surface of a water-insoluble, water-insuspensible solid carrier;
(b) contacting said bound receptor protein with a sample solution containing the unknown HCG to be determined;
(c) allowing sufficient time for an immunochemical reaction between the bound receptor protein and the HCG in the sample solution to take place, to bind the HCG to be determined to the insolubilized HCG receptor protein, forming a first solid phase, and leaving a first liquid phase;
(d) separating the first solid phase from the first liquid phase;
(e) contacting said first solid phase and insolubilized HCG therein with a known amount of a reagent consisting essentially of gold sol dispersion particles having rabbit anti-HCG immunoglobulin attached to their surfaces having a particle size of at least 5 nm;
(f) allowing sufficient time for a second immunological reaction to occur to bind said reagent to that part of said insolubilized HCG which has undergone the reaction in step (c), to form a second solid phase and a second liquid phase;

(g) separating the second solid phase from the second liquid phase; and (h) determining the amount of gold sol in the second solid phase or the second liquid phase, which is a measure of the HCG to be determined in said sample solution.

44. A method as in one of claims 24-35, wherein at least one of said components is drawn from the group consisting of antigens, haptens, and antibodies.

45. A method as in one of claims 24-35, wherein the metal sol dispersion particles are drawn from the group consisting of particles of platinum, gold, silver, copper, silver iodide, silver bromide, copper hydrous oxide, iron hydrous oxide, chromium hydroxide, aluminum hydroxide, aluminum hydrous oxide, chromium hydrous oxide, platinum, silver iodide, iron oxide, aluminum hydroxide, lead sulphide, barium sulfate, titanium dioxide, vanadium oxide, iron hydroxide, arsenic sulphide, manganese hydroxide and mercury sulphide.

46. A method as in claim 45, in which the metal sol dispersion particles are particles of gold.

47. A method as in one of claims 24 to 35, in which said particles are gold, silver, or iron oxide sols.

48. A method as in claim 47, in which said particles range in size from 10–100 nm.

* * * * *

UNITED STATES PATENT AND TRADEMARK OFFICE
CERTIFICATE OF CORRECTION

PATENT NO. : 4,313,734

DATED : Feb. 2, 1982

INVENTOR(S) : Leuvering

Page 1 of 3

It is certified that error appears in the above—identified patent and that said Letters Patent is hereby corrected as shown below:

On page 1, end of first column, there should be added
-- nan: localization of antigens in yeast cell walls", Infect. & Immun., 7, 1973, 487-492. --

Page 1, second column, line 6, change "295,305" to -- 295-305 --;

line 24, change "11-81" to -- 1181 --;

line 54, change "270" to -- 278 --; and after line 54, insert:

-- Garland, J. M., "Preparation and Performance of Gold-labelled Concavalin A For the Location of Specifically Reactive Sites in Walls of S. Faecalis 8191", Electron Microscopy and Cytochemistry (1973), 303-307.

N. Uyeda, et al., "Nucleus Interaction and Fine Structures of Colloidal Gold", J. Colloid and Interface Sci., 43(2), 264-276 (1973). --

On page 2, second column, line 5, cancel "as";

line 6, cancel "known".

Column 2, line 38, change "meal" to -- metal --.

Column 4, line 7, change "proteins" to -- protein --.

UNITED STATES PATENT AND TRADEMARK OFFICE
CERTIFICATE OF CORRECTION

PATENT NO. : 4,313,734

DATED : Feb. 2, 1982

INVENTOR(S) : Leuvering

It is certified that error appears in the above-identified patent and that said Letters Patent are hereby corrected as shown below:

Column 5, line 26, change "coarse" to -- course --.

Column 13, line 42, change "well" to -- wells --.

Column 15, line 7, change "$FeCL_3$" to -- $FeCl_3$ --.

Column 18, line 26, change "in stead" to -- instead --.

Column 21, line 43, cancel ",";
line 44, cancel ",".

Column 22, line 3, cancel ",";
line 56, cancel ",".

Column 23, line 16, cancel ",".

Column 24, line 13, cancel ",";
line 41, change "of" (first occurrence) to -- or --.

Column 25, line 16, cancel ",".

UNITED STATES PATENT AND TRADEMARK OFFICE
CERTIFICATE OF CORRECTION

PATENT NO. : 4,313,734

DATED : Feb. 2, 1982

INVENTOR(S) : Leuvering

It is certified that error appears in the above-identified patent and that said Letters Patent is hereby corrected as shown below:

Column 27, line 50, cancel "and" (second occurrence).

Signed and Sealed this

Twenty-third Day of October 1984

[SEAL]

Attest:

GERALD J. MOSSINGHOFF

Attesting Officer

Commissioner of Patents and Trademarks